United States Patent [19]

Richter

[11] 4,285,721
[45] Aug. 25, 1981

[54] METHOD OF INCREASING THE YIELDS OF SUGAR OBTAINED FROM SUGARCANE

[75] Inventor: Sidney B. Richter, Fairlawn, Ohio

[73] Assignee: Velsicol Chemical Corporation, Chicago, Ill.

[21] Appl. No.: 82,197

[22] Filed: Oct. 5, 1979

[51] Int. Cl.³ ............................................. A01N 43/08
[52] U.S. Cl. ......................................................... 71/88
[58] Field of Search ................................... 71/88, 105

[56] References Cited

U.S. PATENT DOCUMENTS

| | | | |
|---|---|---|---|
| 3,600,407 | 8/1971 | Levin et al. | 71/88 |
| 3,849,108 | 11/1974 | Fields | 71/88 |
| 3,992,186 | 11/1976 | Nickell | 71/88 |

OTHER PUBLICATIONS

Pfeiffer, "Sugar Cane Treatment", (1966), CA 64, p. 16550 g., (1966).
Poulos, "Alkyl 2-methoxy-3,6-dichlorobenzoate etc", (1972), CA 78, No. 68242 w, (1973).
Nickell, "Ripening of Sugarcane by Use, etc", (1976), CA 86, No. 38610 w, (1977).

Primary Examiner—Glennon H. Hollrah
Attorney, Agent, or Firm—Dietmar H. Olesch; Robert J. Schwarz

[57] ABSTRACT

This invention discloses a method of increasing the recoverable sugar in sugar cane which comprises contacting the sugar cane with an effective amount of furfuryl 2-methoxy-3,6-dichlorobenzoate during a late stage of development of the cane.

2 Claims, No Drawings

METHOD OF INCREASING THE YIELDS OF SUGAR OBTAINED FROM SUGARCANE

This invention relates to a method of increasing the yield of sugar obtained from sugarcane. More particularly, this invention relates to a method of increasing the recoverable sugar in sugarcane by treating the sugarcane during its maturation with furfuryl 2-methoxy-3,6-dichlorobenzoate.

A variety of plant growth regulators, stimulants and promotors have been tried in the past in attempts to increase the yields of cultivated crops. These attempts have met with varying success but have generally attained limited commercial significance. One particular crop which has been given increased attention for the purpose of augmenting yields is sugarcane. Accordingly, it is an object of the present invention to provide a new method of increasing the yield of sugar obtained from sugarcane.

Surprisingly, it has been found that the recovery of sugar from sugarcane can be substantially increased through the use of furfuryl 2-methoxy-3,6-dichlorobenzoate. Thus one embodiment of this present invention resides in a method of increasing the recoverable sugar contained in sugarcane which comprises contacting the sugarcane plant with an effective amount of fururyl 2-methoxy-3,6-dichlorobenzoate.

The compound furfuryl 2-methoxy-3,6-dichlorobenzoate is known in the art and is described in U.S. Pat. No. 3,600,407 wherein the compound is disclosed as a herbicide.

To effect the method of this invention, sugarcane is treated at a late stage of development. This treatment is carried out during that stage of development of the sugar cane wherein most of the sugar formation takes place. Thus, under normal growing conditions and common cultivation practices, the furfuryl 2-methoxy-3,6-dichlorobenzoate can be applied to the sugarcane during the period of from about 2 to about 10 weeks before harvesting.

The amount of furfuryl 2-methoxy-3,6-dichlorobenzoate required to effectively increase the recoverable sugar from sugarcane can vary somewhat depending on such factors as the time of application, the weather, crop density, method of application and the like. Generally an amount of at least 0.1 pounds per acre and preferably an amount of from 0.5 pound per acre to about 8.0 pounds per acre can be used. While amounts greater than those mentioned can be used, they will not result in an advantage that would warrant their expense and are therefore not practical. Moreover, if amounts greatly exceeding those described are utilized, damage to the crop may result from the herbicidal action of the furfuryl 2-methoxy-3,6-dichlorobenzoate.

For practical use in treating sugarcane the compound of this invention is generally incorporated into compositions or formulations which comprise an inert carrier and an effective amount of the compound. The compositions enable the active compound to be conveniently applied to the sugarcane at the desired rate. These formulations can be liquid formulations such as emulsifiable concentrates or solutions or solid formulations such as dusts, granules or wettable powders.

The preferred compositions are liquid formulations, particularly emulsifiable concentrates. Emulsifiable concentrates comprise the active compound according to this invention and as the inert carrier, a solvent and an emulsifier. Such emulsifiable concentrates can be extended with water and/or oil to any desired concentration of active compound for application as sprays to the sugar cane. The emulsifier most commonly used in these concentrates are nonionic or mixtures of nonionic with anionic surface-active agents. With the use of some emulsifier systems, an inverted emulsion (water-in-oil) can be prepared.

Typical formulations according to the present invention useful for increasing the recoverable sugar in sugar cane are illustrated in the following examples wherein the quantities are given in parts by weight.

EXAMPLE 1

Preparation of An Emulsifiable Concentrate

The following ingredients are blended thoroughly until a homogeneous liquid concentrate is obtained. This concentrate is mixed with water to give an aqueous dispersion containing the desired concentration of the active ingredients for use as a spray.

| | |
|---|---|
| Furfuryl 2-methoxy-3,6-dichlorobenzoate | 25 |
| Sodium lauryl sulfate | 2 |
| Sodium lignin sulfate | 3 |
| Kerosene | 70 |

EXAMPLE 2

Preparation of a Wettable Powder

The following components are mixed intimately in conventional mixing or blending equipment and are then ground to a powder having a particle size of less than about 50 microns. The finished powder is dispersed in water to give the desired concentration of active compound for application to the sugarcane.

| | |
|---|---|
| Furfuryl 2-methoxy-3,6-dichlorobenzoate | 50 |
| Fuller's earth | 47 |
| Sodium lauryl sulfate | 2.5 |
| Methyl cellulose | 0.5 |

EXAMPLE 3

Preparation of a Dust

The following ingredients are mixed thoroughly and are then ground to an average particle size of less than about 50 microns to give a dust suitable for application with conventional dusting equipment.

| | |
|---|---|
| Furfuryl 2-methoxy-3,6-dichlorobenzoate | 10 |
| Powdered talc | 90 |

The effectiveness of furfuryl 2-methoxy-3,6-dichlorobenzoate for increasing the recoverable sugar in sugar cane was demonstrated in a field test by applying a solution in acetone diluted for application the various indicated application rates. The test compound was applied at each rate on the spindle area of each of 20 stalks of sugarcane in a field in Hawaii, using a syringe with a fine needle as the applicator. A set of 10 of these treated stalks from each group was harvested at 4 and 8 weeks after such treatment. In each harvest a set of 10 untreated stalks were also harvested as a control.

The top 15 joints of the treated cane as well as those of the controls were removed, combined and analyzed for juice purity and pol percent cane (PCC), following the "press method" developed and described by T. Tanimoto, Hawaian Planters Record, 57, 133 (1964). Pol percent cane is a polarimetric determination and equals the percentage of sucrose if the latter is the only substance in the solution which will rotate the plane of polarized light. The pol percent cane is a standard method for determining the sucrose content of sugarcane.

The effectiveness of the compound of this invention for increasing the yield of sugar obtained from sugarcane is demonstrated by the data set out in the following Table I. Repetitive rates with separate control represent duplicative experiments conducted at differing time.

TABLE I

| Rate: Lbs/Acre | Applied 4 weeks Before Harvest | | Applied 8 weeks Before Harvest | |
|---|---|---|---|---|
| | Juice Purity | Pol % Cane | Juice Purity | Pol % Cane |
| 4 | 36.47 | 2.95 | 44.76 | 3.95 |
| 2 | 36.74 | 3.10 | 36.73 | 2.70 |
| 1 | 29.83 | 2.50 | 45.45 | 3.77 |

TABLE I-continued

| Rate: Lbs/Acre | Applied 4 weeks Before Harvest | | Applied 8 weeks Before Harvest | |
|---|---|---|---|---|
| | Juice Purity | Pol % Cane | Juice Purity | Pol % Cane |
| 0.5 | 24.85 | 1.61 | 38.49 | 2.98 |
| 4* | 40.78 | 4.03 | 44.46 | 3.49 |
| 2* | 50.07 | 5.01 | 58.08 | 5.90 |
| 1* | 51.45 | 5.26 | 56.43 | 5.00 |
| 0.5* | 28.74 | 2.11 | 27.22 | 1.75 |
| Control | 34.00 | 2.95 | 37.30 | 2.80 |
| 4 | 72.43 | 7.71 | 59.16 | 5.66 |
| 4* | 84.55 | 10.70 | 84.83 | 11.63 |
| Control | 79.30 | 9.10 | 70.31 | 7.20 |
| 4 | 79.29 | 10.87 | 72.66 | 8.25 |
| Control | 70.42 | 7.44 | 72.06 | 7.87 |
| 1 | 82.90 | 12.05 | 89.19 | 14.76 |
| Control | 80.52 | 9.81 | 83.90 | 11.07 |

*Material applied as an emulsifiable concentrate diluted to the indicated rate

I claim:
1. A method for increasing the recoverable sugar in sugarcane which comprises contacting the sugarcane with an effective amount of furfuryl 2-methoxy-3,6-dichlorobenzoate during the period of from about 2 to about 10 weeks before harvest.
2. The method of claim 1 wherein the sugarcane is contacted with about 0.1 pound to about 8.0 pounds per acre of furfuryl 2-methoxy-3,6-dichlorobenzoate.

* * * * *